(12) United States Patent
Ishikawa et al.

(10) Patent No.: US 10,145,859 B2
(45) Date of Patent: Dec. 4, 2018

(54) AUTOMATIC CONTAINER PROCESSING APPARATUS

(71) Applicant: Kabushiki Kaisha Toshiba, Minato-ku (JP)

(72) Inventors: Misato Ishikawa, Kawasaki (JP); Masato Akita, Kawasaki (JP); Takamitsu Sunaoshi, Yokohama (JP); Takahiro Kokubo, Kamakura (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/687,951

(22) Filed: Aug. 28, 2017

(65) Prior Publication Data

US 2018/0196076 A1  Jul. 12, 2018

(30) Foreign Application Priority Data

Jan. 10, 2017  (JP) ................ 2017-002120

(51) Int. Cl.
*B65G 47/84* (2006.01)
*G01N 35/02* (2006.01)
(Continued)

(52) U.S. Cl.
CPC .............. *G01N 35/026* (2013.01); *B01L 9/06* (2013.01); *B25J 15/0028* (2013.01); *G01N 35/0098* (2013.01); *G01N 35/0099* (2013.01); *G01N 35/025* (2013.01); *G01N 35/04* (2013.01); *B01L 2200/02* (2013.01); *B01L 2300/023* (2013.01); *B01L 2300/0609* (2013.01); *B01L 2300/123* (2013.01); *G01N 2035/00504* (2013.01); *G01N 2035/00574* (2013.01);
(Continued)

(58) Field of Classification Search
CPC ...... B65G 17/20; B65G 17/32; B65G 17/323; B65G 29/00; G01N 35/0099; G01N 35/10; G01N 33/5302; G01N 33/48; B25J 15/0028; B25J 15/08; B25J 15/103
USPC .................... 198/470.1, 474.1, 476.1, 478.1
See application file for complete search history.

(56) References Cited

U.S. PATENT DOCUMENTS 3,038,340 A    6/1962  Isreeli
3,175,702 A *  3/1965  Banyas ................ C03B 35/125
                                                198/476.1

(Continued)

FOREIGN PATENT DOCUMENTS

JP    2-156141   6/1990
JP    3091988    9/2000
(Continued)

OTHER PUBLICATIONS

Extended Search Report dated Feb. 9, 2018 in European Patent Application No. 17187697.2.

*Primary Examiner* — James R Bidwell
(74) *Attorney, Agent, or Firm* — Oblon, McClelland, Maier & Neustadt, L.L.P.

(57) ABSTRACT

According to one embodiment, an automatic container processing apparatus includes a tube socket, an operation part, and a control device. The tube socket has a container holding part for holding a container. The operation part is capable of operating the container holding part of the tube socket. The control device controls the operation part. The container held by the container holding part is dropped by operating the operation part.

13 Claims, 9 Drawing Sheets

(51) Int. Cl.
   *G01N 35/00*        (2006.01)
   *B01L 9/06*          (2006.01)
   *B25J 15/00*       (2006.01)
   *G01N 35/04*       (2006.01)

(52) U.S. Cl.
   CPC ............ *G01N 2035/0406* (2013.01); *G01N 2035/0439* (2013.01); *G01N 2035/0455* (2013.01); *G01N 2035/0474* (2013.01)

(56) References Cited

U.S. PATENT DOCUMENTS

| | | | |
|---|---|---|---|
| 4,647,432 A | 3/1987 | Wakatake | |
| 4,824,641 A | 4/1989 | Williams | |
| 5,492,023 A | 2/1996 | Kitamura et al. | |
| 5,607,045 A * | 3/1997 | Hermann Kronseder | B08B 9/42 |
| | | | 198/476.1 |
| 6,746,648 B1 | 6/2004 | Mattila et al. | |
| 6,938,753 B2 * | 9/2005 | Bonatti | B65G 47/847 |
| | | | 198/470.1 |
| 8,469,179 B2 * | 6/2013 | Balzarin | B67C 3/242 |
| | | | 198/474.1 |
| 8,956,149 B2 * | 2/2015 | Zacche | B29C 49/4205 |
| | | | 198/470.1 |
| 2003/0034227 A1 * | 2/2003 | Gerber | B65G 47/847 |
| | | | 198/473.1 |
| 2004/0219678 A1 | 11/2004 | Mattila et al. | |
| 2005/0011730 A1 * | 1/2005 | Wittmann | B65G 47/847 |
| | | | 198/470.1 |
| 2008/0044908 A1 | 2/2008 | Jacobs et al. | |
| 2009/0202334 A1 | 8/2009 | Mattila et al. | |
| 2010/0291619 A1 | 11/2010 | Robinson et al. | |
| 2010/0311108 A1 | 12/2010 | Bishop et al. | |
| 2011/0124028 A1 | 5/2011 | Robinson et al. | |
| 2011/0124029 A1 | 5/2011 | Remes et al. | |
| 2011/0124030 A1 | 5/2011 | Philipak et al. | |
| 2011/0124038 A1 | 5/2011 | Bishop et al. | |
| 2011/0124096 A1 | 5/2011 | Philipak et al. | |
| 2011/0125314 A1 | 5/2011 | Robinson et al. | |
| 2015/0031074 A1 | 1/2015 | Robinson et al. | |
| 2015/0176046 A1 | 6/2015 | Robinson et al. | |
| 2016/0154017 A1 | 6/2016 | Oguri et al. | |

FOREIGN PATENT DOCUMENTS

| | | |
|---|---|---|
| JP | 2007-322394 | 12/2007 |
| JP | 5467954 | 4/2014 |
| JP | 2014-233765 | 12/2014 |

\* cited by examiner

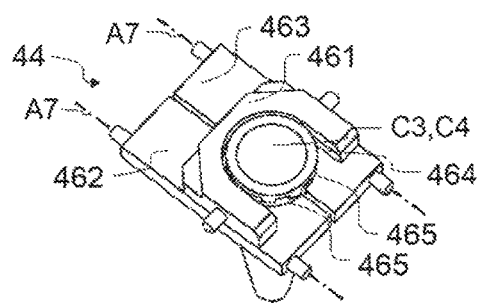
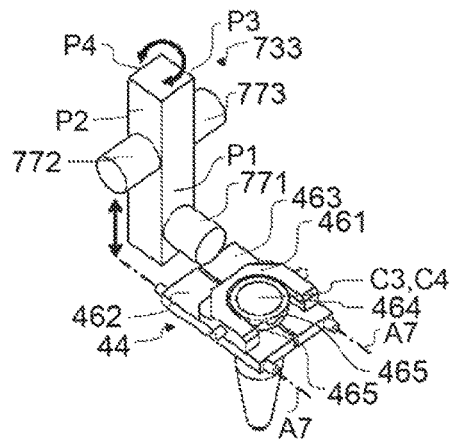
FIG. 15A  FIG. 15B
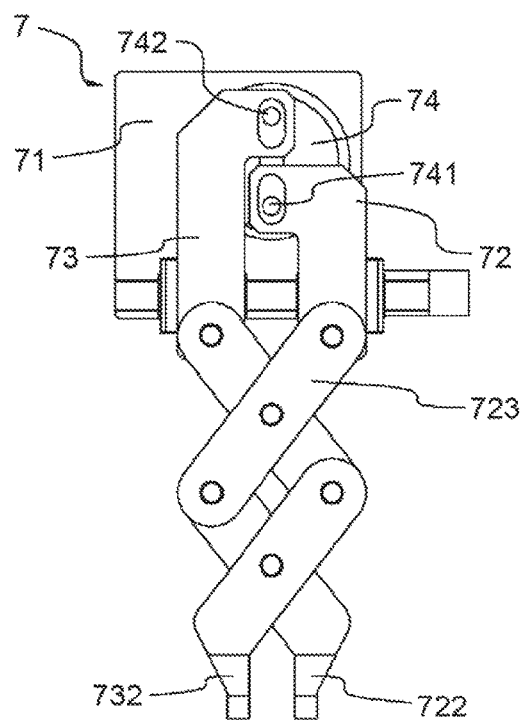
FIG. 16

AUTOMATIC CONTAINER PROCESSING APPARATUS

CROSS-REFERENCE TO RELATED APPLICATION

This application is based upon and claims the benefit of priority from Japanese Patent Application No. 2017-002120, filed on Jan. 10, 2017; the entire contents of which are incorporated herein by reference.

FIELD

Embodiments described herein relate generally to an automatic container processing apparatus.

BACKGROUND

A specimen processing system is a system that automation processing is implemented by arranging individual units having a plurality of functions and conveying containers containing specimens between the units. Such system is generally large in size, but the installation space is restricted, and it is required to downsize the system.

Recently, the system has been downsized by employing a double annular processing mechanism in which containers containing specimens are annularly arranged an inner side and an outer side. In the double annular processing mechanism, when the used containers installed at the inner side of the annular processing mechanism are disposed, the containers are disposed after passing over the outer side of the annular processing mechanism, and the risk of contamination due to dropping droplets from the containers can occur.

BRIEF DESCRIPTION OF THE DRAWINGS

FIGS. 15A and 15B are diagrams schematically showing a tube holding part of an automatic container processing apparatus according to a third embodiment.

FIG. 16 is a diagram schematically showing a holding knob operation part of an automatic container processing apparatus according to a fourth embodiment.

DETAILED DESCRIPTION

Figure 1:
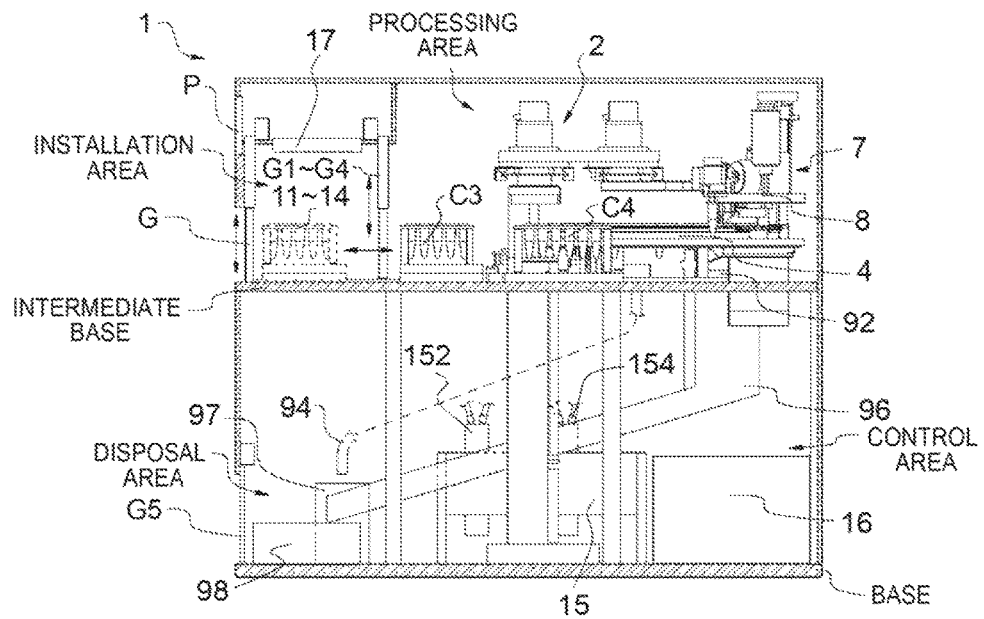
FIG. 1 is a cross-sectional view of an automatic container processing apparatus according to a first embodiment when viewed from a lateral direction.

According to one embodiment, an automatic container processing apparatus includes a tube socket, an operation part, and a control device. The tube socket has a container holding part for holding a container. The operation part is capable of operating the container holding part of the tube socket. The control device controls the operation part. The container held by the container holding part is dropped by operating the operation part.

Hereinafter, an automatic container processing apparatus according to embodiments will be described with reference to the drawings. Same reference signs indicate similar parts. The drawings are merely schematic or conceptual, and the relation between the thickness and the width of each part and the ratio coefficient of the size between parts are not necessarily the same as the actual ones. Although the same part is indicated, the dimensions and ratio coefficients of the parts can be different from each other depending on the drawing.

First Embodiment

An automatic container processing apparatus according to a first embodiment will be described with reference to FIGS. 1 to 13.

Figure 2:
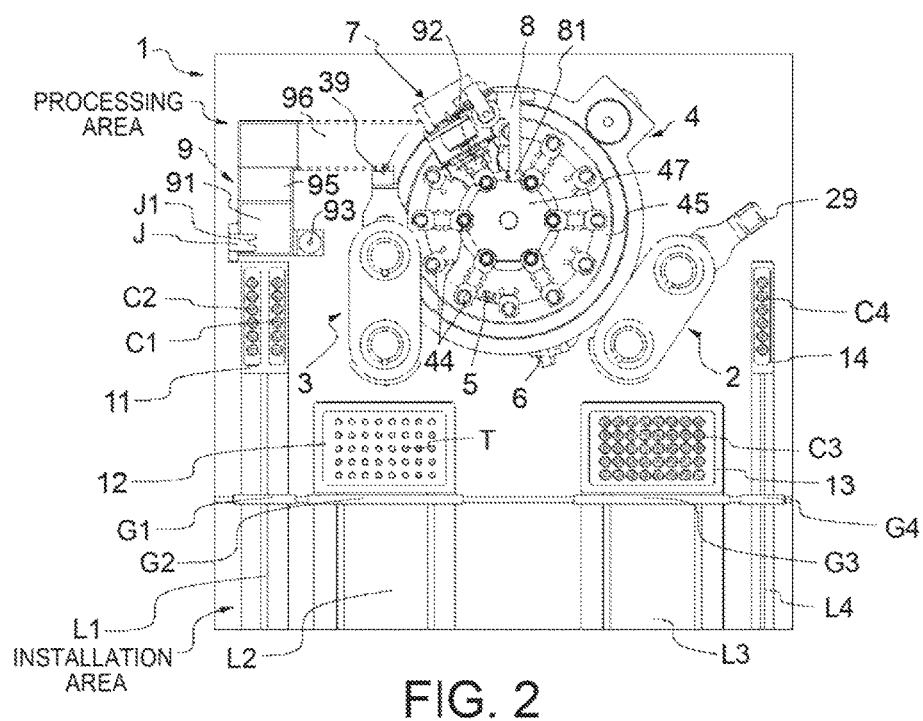
FIG. 2 is a top view of a processing area of the automatic container processing apparatus according to the first embodiment when viewed from above.

FIG. 1 is a cross-sectional view of the automatic container processing apparatus according to the first embodiment when viewed from a lateral direction. FIG. 2 is a top view of a processing area of the automatic container processing apparatus according to the first embodiment when viewed from above.

As shown in FIG. 1, an automatic container processing apparatus 1 is divided from an intermediate base into an upper layer and a lower layer. The upper layer is provided on the intermediate base, and includes an installation area (also referred to as a first area) and a processing area (also referred to as a second area). The lower layer is provided on a base, and includes a disposal area (also referred to as a third area) and a control area (also referred to as a fourth area). The automatic container processing apparatus 1 conveys a plurality of cartridges installed at the installation area to the processing area, and processes the specimen in a tube loaded in the cartridge at the processing area. Then, the processed specimen is collected from the tube, and the collected tube is disposed at the disposal area.

As shown in FIGS. 1 and 2, at the installation area of the automatic container processing apparatus 1, a conveyance cartridge 11 (also referred to as a first cartridge) for loading a plurality of collection containers and specimen containers, a tip cartridge 12 (also referred to as a second cartridge) for loading a plurality of tips, a centrifuge tube cartridge 13

(also referred to as a third cartridge) for loading a plurality of centrifuge tubes, and a magnetic bead tube cartridge 14 (also referred to as a fourth cartridge) for loading a plurality of magnetic bead tubes containing magnetic beads therein, are installed. Each cartridge is placed on a cartridge conveying mechanism (not shown), passes on guide rails (also referred to as first to fourth guide rails), and is conveyed to the processing area. At the boundary between the installation area and the processing area, gates are provided (also referred to as first to fourth gates).

At the processing area, a tube arm 2, a pipettor arm 3, a rotary tube socket 4 which rotationally drives about a rotation shaft, a magnetic separator 5, a stirrer 6, a holding knob operation part 7, a dispensing arm 8, and a disposal part 9 are positioned.

At the disposal area, a disposal duct and a disposal pipe connected with the disposal part 9, a collection box for collecting wastes, a waste liquid tank for storing a waste liquid, and the like are positioned.

At the control area, a liquid transporting part 15 including a cylinder pump for pipettor and the like, and a control device 16 are positioned.

First, the installation area will be described in detail. The installation area is airtightly partitioned by a gate opening and closing mechanism, and includes an installation gate G between the installation area and the outside of the apparatus, and the first to fourth gates between the installation area and the processing area. The installation area includes a sterilizer 17 to ensure sterility compared to the outside of the apparatus. The cartridges carried in from the installation gate G are placed on a cartridge transport mechanism (not shown). Then, the cartridges pass on the guide rails and are carried into the processing area through the first to fourth gates.

More specifically the first cartridge 11 passes on a first guide rail L1 and is carried in or out between the installation area and the processing area through a first processing gate G1. Similarly, the second cartridge 12 passes on a second guide rail L2 and is carried in or out between the installation area and the processing area through a second processing gate G2. The third cartridge 13 passes on a third guide rail L3 and is carried in or out between the installation area and the processing area through a third processing gate G3. The fourth cartridge 14 passes on a fourth guide rail L4 and is carried in or out between the installation area and the processing area through a fourth processing gate G4.

The first to fourth cartridges are capable of loading, for example, a plurality of containers or tips, and the containers or the like can be taken out from above. The first to fourth guide rails are installed on the intermediate base. The first to fourth guide rails connect the installation area with the processing area, and guide the cartridges placed on the cartridge conveying mechanism to the processing area. The cartridge conveying mechanism is, for example, a linear motion mechanism having a motor, and moves on the guide rail. When each cartridge is carried in the processing area, each of the first to fourth gates is opened by an opening/closing mechanism (not shorn), and each cartridge is carried in the processing area. The installation gate G and the first to fourth gates may be operated by an operator (also referred to as a user) through an operation panel P installed on, for example, the outer surface of the automatic container processing apparatus 1.

A plurality of specimen containers C1 containing specimens and a plurality of collection containers C2 for collecting processed specimens are loaded in the first cartridge 11. A plurality of tips T is loaded in the second cartridge 12. The tip T is attached to the tip of a pipettor which dispenses a solution, and the replacement of the tip T prevents contamination of the specimen. A plurality of centrifugal tubes C3 is loaded in the third cartridge 13. The centrifugal tube C3 is a vessel having an opening at the upper part and for containing the specimen. A plurality of magnetic bead tubes C4 is loaded in the fourth cartridge 14. Processing with less contamination compared to separation by gravity can be performed with magnetic beads since the beads are gathered by the magnetic force of a permanent magnet. The tube shapes of the centrifugal tube C3 and the magnetic bead tube C4 are substantially the same. The centrifugal tube C3 and the magnetic bead tube C4 can be collectively referred to as a tube.

Next, the processing area will be described in detail. The processing area is an area for processing specimen containers and the like loaded in the cartridges.

At the processing area, a tube arm 2, a pipettor arm 3, a rotary tube socket 4 which rotationally drives about a rotation shaft, a magnetic separator 5, a stirrer 6, a holding knob operation part 7, a dispensing arm 8, and a disposal part 9 are positioned.

The tube arm 2 installs the centrifugal tubes C3 loaded in the third cartridge 13 or the magnetic bead tubes C4 loaded in the fourth cartridge 14, to the rotary tube socket 4.

Figure 3A:
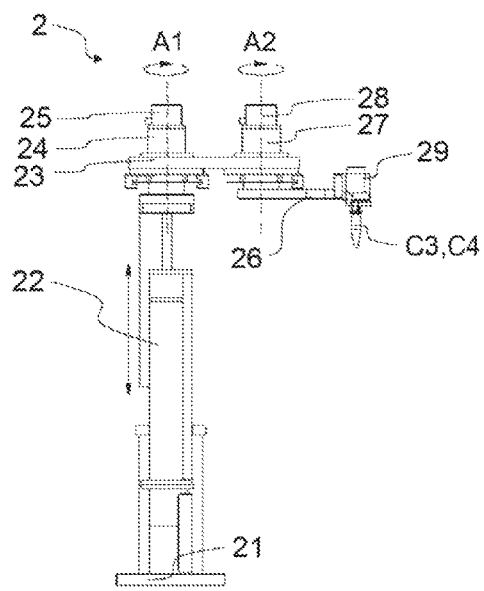
FIGS. 3A and 3B are schematic view showing n example of a tube arm and a pipettor arm.

FIG. 3A is a schematic diagram showing an example of the tube arm 2. As shown in FIG. 3A, the tube arm 2 includes a tube arm base 21, a first linear motion mechanism 22, a first link 23, a first motor 24, a first encoder 25, a second link 26, a second motor 27, a second encoder 28, and a first holding mechanism 29.

The tube arm base 21 is installed on the base. The first linear motion mechanism 22 has a lower end connected with the tube arm base 21 and an upper end connected with the first link 23. The first linear motion mechanism 22 moves the first link 23 in a height direction which is the direction perpendicular to the intermediate base. The first linear motion mechanism 22 has a linear motion motor. The first motor 24 is connected with the base end of the first link 23. For example, a bearing (not shown) is attached between the first motor 24 and the first link 23 and the rotation shaft of the first motor 24 is connected with the upper end of the first linear motion mechanism 22. The first link 23 rotationally drives about a first rotation shaft A1 of the first motor 24 in a horizontal plane substantially parallel to the intermediate base. The first motor 24 is provided with the first encoder 25 for measuring the rotation angle. It is preferable that the direction of the first rotation shaft A1 and the drive direction of the first linear motion mechanism 22 are substantially parallel.

The second motor 27 is installed at the end of the first link 23. The second motor 27 is provided with the second encoder 28 for measuring the rotation angle. For example, a bearing (not shown) is attached between the rotation shaft of the second motor 27 and the first link 23, and the base end of the second link 26 is connected with the rotation shaft of the second motor 27. The second link 26 rotationally drives about a second rotation shaft A2 of the second motor 27 in a plane substantially parallel to the intermediate base. It is preferable that the planes in which the first link 23 and the second link 26 rotationally drive are substantially parallel.

A first holding mechanism 29 for holding the centrifugal tube or the magnetic bead tube is connected with the end of the second link 26. The first holding mechanism 29 may be formed of, for example, two rod bodies capable of opening and closing and hold the inner diameter part of the centrifugal tube or the magnetic bead tube by opening the rod bodies. The tube may be held by a knob (not shown) or the like installed at the first holding mechanism.

The tube arm base 21 or the first linear motion mechanism 22 pierces the intermediate base and supports the first link 23, the second link 26, and the like in the processing area.

The tube arm 2 is connected with the control device 16 which will be described later, and the driving of the first linear motion mechanism 22, the first motor 24, the second motor 27, and the first holding mechanism 29 is controlled.

Figure 3B:
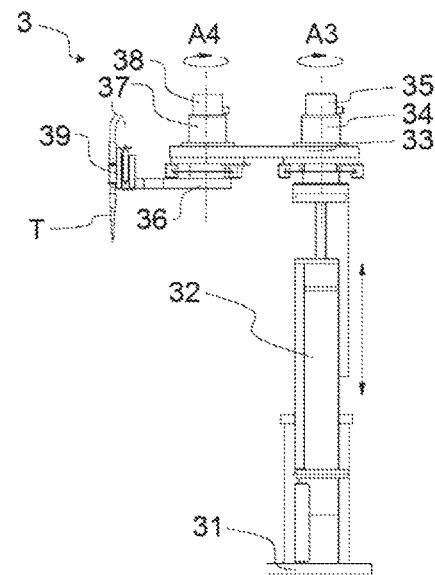

FIG. 3B is a schematic diagram showing an example of the pipettor arm 3. The pipettor arm 3 attaches the tip T loaded in the second cartridge 12 to the tip of a pipettor's nozzle. Then, the tip and the pipettor's nozzle extract the specimen from the specimen container loaded in the first cartridge and inject it into the tube installed at the rotary tube socket.

The pipettor arm 3 sucks the processed specimen from the centrifugal tube C3 at the rotary tube socket 4 and injects it into the collection container C2 loaded in the first cartridge 11.

As shown in FIG. 3B, the pipettor arm 3 includes a pipettor arm base 31, a second linear motion mechanism 32, a third link 33, a third motor 34, a third encoder 35, a fourth link 36, a fourth motor 37, a fourth encoder 38, and a pipettor's nozzle 39.

The pipettor arm base 31 is installed on the base. The second linear motion mechanism 32 has a lower end connected with the pipettor arm base 31 and an upper end connected with the third link 33. The second linear motion mechanism 32 moves the third link 33 in a height direction which is the direction perpendicular to the intermediate base. The second linear motion mechanism 32 has a linear motion motor. The third motor 34 is connected with the base end of the third link 33. For example, a bearing (not shown) is attached between the third motor 34 and the third link 33, and the rotation shaft of the third motor 34 is connected with the upper end of the second linear motion mechanism 32. The third link 33 rotationally drives about a third rotation shaft A3 of the third motor 34 in a horizontal plane substantially parallel to the intermediate base. The third motor 34 is provided with the third encoder 35 for measuring the rotation angle. It is preferable that the axial direction of the third rotation shaft A3 and the driving direction of the second linear motion mechanism are substantially parallel.

The fourth motor 37 is installed at the end of the third link 33. The fourth motor 37 is provided with the fourth encoder 38 for measuring the rotation angle. For example, a bearing (not shown) is attached between the rotation shaft of the fourth motor 37 and the third link 33, and the base end of the fourth link 36 is connected with the rotating shaft of the fourth motor 37. The fourth link 36 rotationally drives about a fourth rotation shaft A4 of the fourth motor 37 in a plane substantially parallel to the intermediate base. It is preferable that the planes in which the third link 33 and the fourth link 36 rotationally drive are substantially parallel.

The pipettor's nozzle 39 is connected with the end of the fourth link 36. A cylinder pump for pipettor is connected with the pipettor's nozzle 39 to change the pressure inside the pipettor. The specimen is sucked or discharged by the motion of this cylinder pump for pipettor.

The tip T may be attached to the pipettor's nozzle 39 by pressing the pipettor's nozzle 39 against the tip T from the vertical direction to fit the nozzle. For example, the pipettor arm 3 is driven to move the pipettor's nozzle 39 above the second cartridge 12 to be loaded with the tip T. Then, by driving the second linear motion mechanism 32, the pipettor's nozzle 39 is lowered and pressed against the tip T from the vertical direction and fitted to the tip T.

For example, a hollow protrusion (not shown) may be provided at the pipettor's nozzle 39, and the pipettor's nozzle 39 may be fitted by pressing the protrusion against the inner diameter part of the tip. To remove the tip T from the pipettor's nozzle 39, the tip T is removed with a tip removing jig J (see FIG. 2). The tip removing jig J is, for example, a plate body provided with a notch J1 according to the shape of the protrusion, and the notch J1 is inserted from the side of the protrusion to the fitting part. By moving the second linear motion mechanism 32 upward in this state, the edge of the tip T comes in contact with the tip removing jig J and the tip T is removed. The tip removing jig J is preferably provided in the vicinity of a first disposal port, which will be described later, for disposing the tip T.

When the protrusion can be protruded and retracted in the vertical direction, the protrusion is being protruded to attach the tip T. In order to remove and dispose the tip T, the tip T may be removed by retracting the protrusion fitted with the tip T into the pipettor's nozzle 39 to bring the outer edge of the pipettor's nozzle 39 in contact with the edge of the tip T. In this case, it is possible to remove the tip without the tip removing jig J.

The pipettor arm base 31 or the second linear motion mechanism 32 pierces the intermediate base and supports the third link 33, the fourth link 36, and the like in the processing area.

The pipettor arm 3 is connected with the control device 16 which will be described later, and the driving of the second linear motion mechanism 32, the third motor 34, the fourth motor 37, the pipettor's nozzle 39, and the cylinder pump for pipettor is controlled.

The rotary tube socket 4 rotates and processes the tube containing the specimen attached by the tube arm 2.

Figure 4:
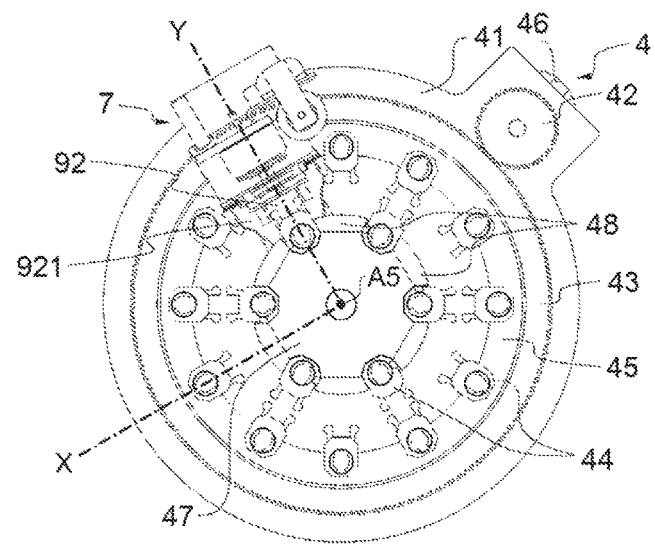
FIG. 4 is a schematic view showing an example of a rotary tube socket.

FIG. 4 is a schematic views showing an example of the rotary tube socket 4. As shown in FIG. 4, the rotary tube socket 4 includes a tube socket base 41, a first gear 42, a second gear 43, a plurality of tube holding parts 44 (also referred to as container holding parts), a socket ring 45 which supports the tube holding parts 44, a fifth motor 46, and a centrifugal separator 47 positioned at the inner side of the socket ring and having a plurality of tube holding parts 44.

The rotary tube socket 4 is an annular socket having the tube holding parts 44 for holding the centrifugal tubes C3 or the magnetic bead tubes C4. The second gear 43 is provided on the socket base 41 via the first gear 42 and a bearing (not shown). The first gear 42 is rotated by the fifth motor 46, and the socket ring 45 on the second gear 43 engaging with the first gear 42 is thereby rotated. The socket ring 45 is provided with the tube holding parts 44. The magnetic bead tubes C4 held by the tube holding parts 44 rotate about a fifth rotation shaft A5 which is the center of the rotary tube socket 4. The centrifugal separator 47 is arranged at the inner side of the socket ring 45. The centrifugal separator 47 has, on the outer circumferential part, the tube holding parts 44 for holding the centrifugal tubes C3. Stoppers 48 are provided on both sides of each tube holding part 44 of the centrifugal separator 47. The centrifugal separator 47 includes a sixth motor and a sixth encoder (not shown). The centrifugal tubes C3 held by the tube holding parts 44 of the centrifugal separator 47 rotate about the rotation shaft which is substantially the same as the fifth rotation shaft A5. In other words, the rotary tube socket 4 has a double structure of the centrifugal separator 47 which rotates the tube holding parts about the fifth rotation shaft A5 at the inner circumferential part, and the socket ring 45 which rotates the tube holding parts at the outer circumferential part. It is preferable that the heights of the tube holding parts 44 supported by the socket ring 45 and the tube holding parts 44 arranged in the centrifugal separator 47 are substantially equal. For example, at the centrifugal separator 47, six tube holding parts 44 are installed at equal intervals in an annular shape. At the socket ring 45, twelve tube holding parts 44 are installed at equal intervals in an annular shape. The number of tube holding parts is not limited to this number, and can be appropriately changed according to the scale of the automatic container processing apparatus 1. The centrifugal separator 47 and the socket ring 45 can separately rotate.

The magnetic bead tube C4 is installed at the tube holding part 44 of the socket ring 45 by the tube arm 2. The centrifugal tube C3 is installed at the tube holding part 44 of the centrifugal separator 47 by the tube arm 2.

Figure 5:
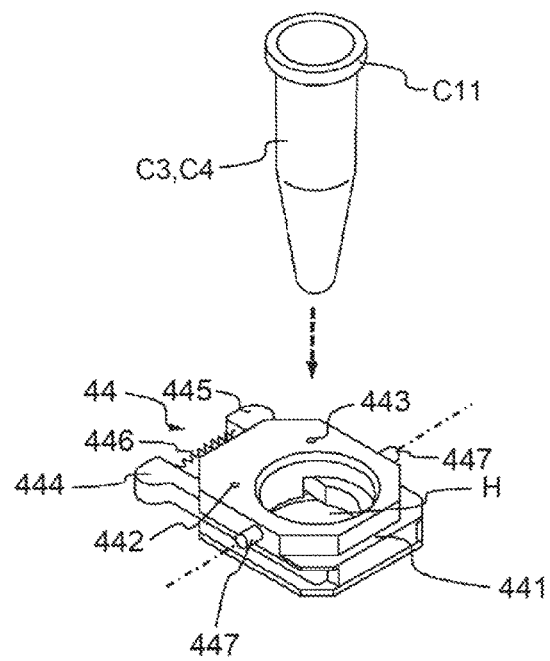
FIG. 5 is a perspective view showing an example of a tube holding part.

FIG. 5 is a perspective view showing an example of the tube holding part 44. As shown in FIG. 5, the tube holding part 44 includes a holder 441 into which the centrifugal tube C3 or the magnetic bead tube C4 is inserted, and two holding knob rotation shafts 442 and 443, two holding knobs 444 and 445 which are rotatable about each rotation shaft, and an elastic part 446 connecting between the two holding knobs. A shaft 447 is provided at the holder 441 installed at the centrifugal separator 47, and the tube holding part 44 is rotatable about the shaft 447. The direction of the shaft 447 is substantially parallel to the rotation direction of the centrifugal separator 47 and is perpendicular to the radial direction of the centrifugal separator 47. The elastic part 446 may be a spring, rubber, or the like.

The holder 441 includes a hole H for inserting a tube and the two holding knobs 444 and 445 at the lower part. The two holding knobs 444 and 445 are installed respectively at the two holding knob rotation shafts 442 and 443 installed at the holder 441, and rotate respectively about the holding knob rotation shafts 442 and 443. The two holding knobs 444 and 445 are connected by the elastic part 446, and the elastic part 446 energizes the holding knobs so as to rotate in the opposite direction to each other. That is, the elastic part 446 energizes the two holding knobs in the direction separating them from each other. Thus, the sides of the two holding knobs 444 and 445 at which a tube is held approach, and thereby sandwich and hold the tube. In the holding knob, the part at the side where the elastic part 446 is positioned may be referred to as a knob part, and the side at which the tube is held may be referred to as a holding part.

Figure 6:
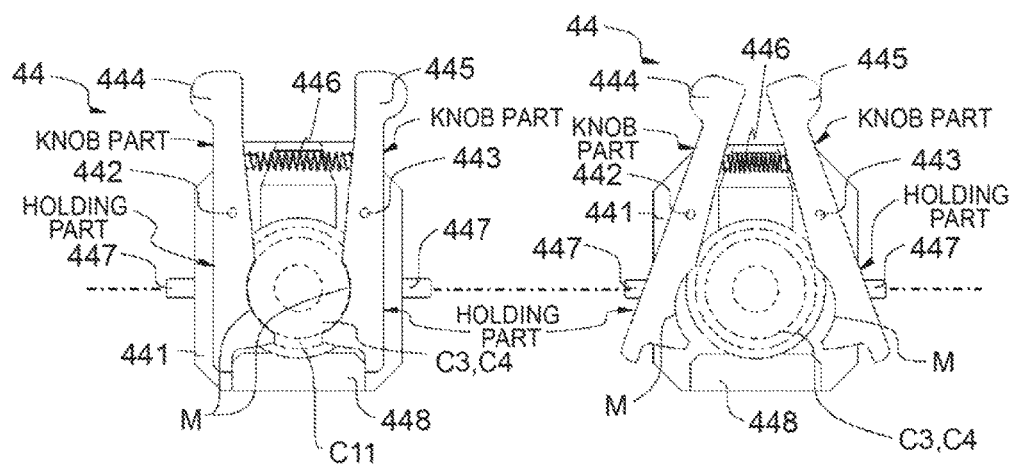
FIG. 6 is a view showing an example of opening and closing operations of the tube holding part.

FIG. 6 is a view showing an example of opening and closing operations of the tube holding part 44. The left side of FIG. 6 is a view showing a closing operation of the tube holding part 44. As shown in the left side of FIG. 6, in the closing operation, the tube indicated by the broken line is sandwiched and held between the two holding knobs. The elastic part 446 is arranged so that the holding knob rotation shafts 442 and 443 are positioned between the elastic part 446 and the tube. It is preferable that the two holding knobs each have an arcuate groove M according to the shape of the tube so that the tube can be stably held, and that an outer edge C11 of the tube having a larger diameter than the grooves M is held so as to be placed on the holding part. In order to secure the diameter of the hole H while a tube is not being inserted, the closing operation is restricted by a protrusion 448 provided at the holder 441 so that the sides opposite to the knob parts of the holding parts are not closed. When holding a tube, the grooves M in contact with the tube are positioned inside the two holding knob rotation shafts 442 and 443. When centrifugal force applies to the tube, the force received by the holding knobs from the tube acts as the moment about the holding knob rotation shaft, but the direction of this moment is the direction of closing the holding knobs, and the centrifuge tube can be more reliably held.

The right side of FIG. 6 is a view showing an opening operation of the tube holding part 44. As shown in the right side of FIG. 6, when the two holding knobs 444 and 445 are energized in a direction in which the elastic part 446 shrinks, the holding knobs sandwiching the tube are opened, and the tube is dropped downward from the holder. In order for the two holding knobs to be the state of the right side of FIG. 6, a holding knob operation part 7 which will be described later is used.

The tube holding parts 44 installed at the centrifugal separator 47 are arranged so that the two holding knobs face the direction of the socket ring 45 which is the outside of the centrifugal separator 47. The tube holding parts 44 installed at the socket ring 45 are arranged so that the two holding knobs face the direction of the centrifugal separator 47 which is the inner side of the socket ring. In other words, the tube holding parts 44 arranged at the centrifugal separator 47 and the socket ring 45 are arranged so that holding knobs face each other.

Figure 7:
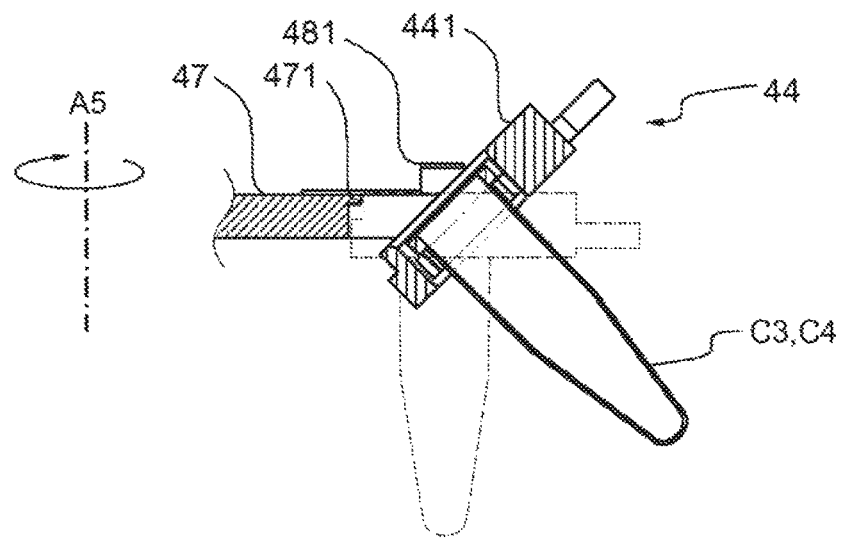
FIG. 7 is a cross-sectional view showing an example of a tube held by the tube holding part when a centrifugal separator is rotating.

FIG. 7 is a cross-sectional view showing an example of the centrifugal tube C3 held by the tube holding part 44 when the centrifugal separator 47 is rotating.

As shown in FIG. 7, when the centrifugal separator 47 is rotating, the centrifugal force is generated at the centrifugal tube C3 and the tube holding part 44. The direction of the centrifugal force is generated at the outer side of the radial direction of the centrifugal separator 47. In order to prevent the influence of the centrifugal force, the tube holding part 44 of the present embodiment is rotatable about the shaft 447 provided at the holder 441. As shown in FIG. 7, when the centrifugal force is generated at the centrifugal tube C3, the centrifugal tube C3 and the tube holding part 44 rotate about the shaft 447 and incline so that the opening of the centrifugal tube C3 faces the direction of the rotation shaft (the fifth rotation shaft) A5 of the centrifugal separator 47. Thus, the lower end of the centrifugal tube inclines and faces outward, and the specimen in the centrifugal tube is prevented from jumping out of the centrifugal tube due to the centrifugal force. Furthermore, the holder 441 comes in contact with a protrusion 481 of the tube holding part stopper 48 provided on the upper surface of the centrifugal separator 47, and the inclination of the tube holding part 44 and the centrifugal tube C3 is thereby restricted so as to be a predetermined angle or less. When the centrifugal separator 47 is stopped and the inclined tube holding part 44 returns to the horizontal position, a protrusion 471 of the centrifugal separator 47 comes in contact with the tube holding part 44, and the inclination of the tube holding part 44 and the centrifugal tube C3 is thereby restricted so as to be a predetermined angle or less.

The magnetic separator 5 applies a magnetic field to the specimen in the magnetic bead tube C4 containing magnetic beads and causes the magnetic beads to be gathered in the direction of the magnetic field together with unnecessary substances in the specimen. The specimen solution remaining separated from the magnetic beads is sucked by the tip T attached to the pipettor's nozzle 39. The magnetic separator 5 is arranged in the vicinity of the magnetic bead tube C4 installed at the tube holding part 44 of the socket ring 45 (see FIG. 2). For example, it is preferable that magnetic separator 5 is arranged below the magnetic bead tube C4. By applying a magnetic field from the lower side of the magnetic bead tube C4 by the magnetic separator, the magnetic beads are gathered in the lower part of the tube and the specimen solution from which the unnecessary substances are eliminated remains on the top, and the specimen solution is thereby easily sucked with the pipettor. The magnetic separator 5 may be a permanent magnet, a hollow solenoid type electromagnet, or the like.

The stirrer 6 stirs the magnetic beads in the magnetic bead tube C4 and the injected specimen. By stirring the magnetic beads and the specimen solution, unnecessary substances in the specimen solution are mixed with the magnetic beads so that the unnecessary substances can be efficiently taken into the magnetic beads when a magnetic field is applied. The stirrer 6 is arranged at a position where vibration can be applied to the magnetic bead tube C4 (see FIG. 2) It is preferable that the stirrer 6 is arranged in the vicinity of the magnetic separator 5. The stirrer 6 may be a shaker, a vibrator, or the like.

Figure 8:
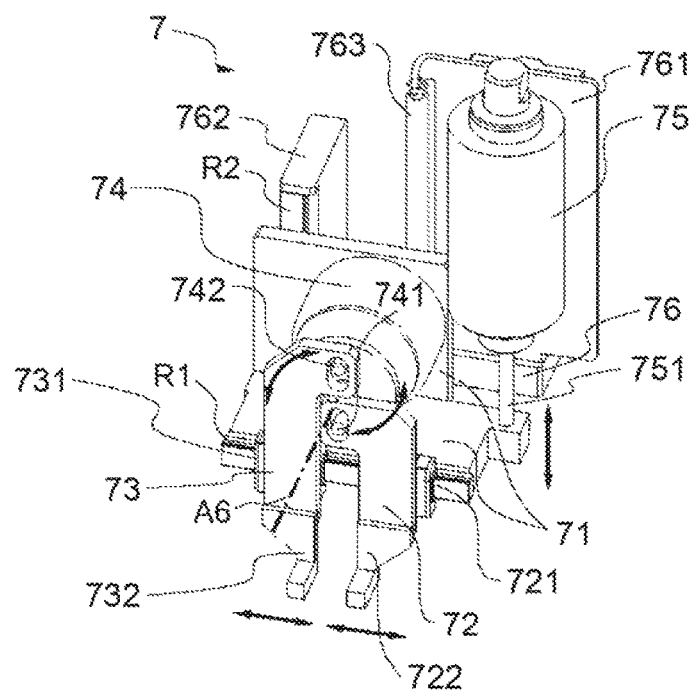
FIG. 8 is a schematic diagram showing an example of a holding knob operation part.

FIG. 8 is a schematic view showing an example of the holding knob operation part 7. As shown in FIG. 8, the holding knob operation part 7 includes a holding mechanism base 71, a first holding link 72, a second holding link 73, a rotary solenoid 74, a translation solenoid 75, and a support column 76.

The holding knob operation part 7 is positioned above both tube holding parts 44 of the centrifugal separator 47 and of the socket ring 45 of the rotary tube socket 4.

The L-shaped holding mechanism base 71 formed of two surfaces of a vertical surface and a horizontal surface includes the rotary solenoid 74 on the vertical surface and a first rail R1 on the horizontal surface. The first rail R1 is connected with a first holding link guide 721 of the first holding link 72 and guides the first holding link 72 in the horizontal direction. The first rail R1 is further connected with a second holding link guide 731 of the second holding link 73 and guides the second holding link 73 in the horizontal direction.

A first holding arm 722 is provided at the end of the first holding link 72. A second holding arm 732 is provided at the end of the second holding link 73.

The rotary solenoid 74 has a first positioning part 741 and a second positioning part 742. The first positioning part 741 is attached to an elliptical hole provided at the base end of the first holding link 72, and the second positioning part 742 is attached to an elliptical hole provided at the base end of the second holding link 73. The first holding link 72 and the second holding link 73 are attached so as to face the vertical direction. As shown in FIG. 8, the first positioning part 741 and the second positioning part 742 are aligned in the vertical direction when the holding arms are in a closing state. The "closing state" of the holding arms is a state that the distance between the first holding arm 722 and the second holding arm 732 is the closest to hold an object. On the other hand, an "opening state" of the holding arms is a state that the distance between the first holding arm 722 and the second holding arm 732 is separated not to hold the object. The rotary solenoid 74 can be driven about a sixth rotation shaft A6 clockwise (CW) or counterclockwise (CCW). In the case of FIG. 8, when the rotary solenoid 74 is driven in the CCW direction, the first holding link 72 and the second holding link 73 move away from each other. That is, the holding arms are in the opening state. When the rotary solenoid is driven in the CW direction from this state, the first holding link 72 and the second holing link 73 move towards each other. That is, the holding arms are in the closing state. The holding knob operation part 7 holds the knob parts of the holding knobs 444 and 445 of the tube holding part 44 by the opening and closing operations of the first holding link 72 and the second holding link 73.

The translation solenoid 75 is supported by a support plate 761 fixed to the support column 76. The translation solenoid 75 has a function for changing the height of the holding mechanism base 71 by driving upward and downward in the height direction. That is, the translation solenoid 75 changes the heights of the first holding link 72 and the second holding link 73. The holding mechanism base 71 is connected with one end of a tension spring 763 of which the other end is connected with the support plate 761. The holding mechanism base 71 is lowered by being pushed downward by a pushing in-pulling out rod 751 of the translation solenoid 75, and raised by the pullback of the pushing in-pulling out rod 751 and the restoring force of the tension spring 763. A support block 762 fixed to the support column 76 is provided with a second rail R2 which guides the holding mechanism base 71 in the vertical direction, and is connected with a link guide (not shown) provided at the holding mechanism base 71. The holding mechanism base 71 moves along the second rail R2 in the vertical direction according to the driving of the translation solenoid 75.

The first holding link 72 and the second holding link 73 are driven upward and downward by the translation solenoid 75, and further driven in the lateral direction by the rotary solenoid 74 to open and close the first holding arm 722 and the second holding arm 732. In order to dispose the tube, the holding knob operation part 7 lowers the holding arms to the height of the tube holding part while the first holding arm 722 and the second holding arm 732 are being opened. Then, by closing the first holding arm 722 and the second holding arm 732, and by opening the holding parts of the holding knobs 444 and 445 of the tube holding part to the state of the right side of FIG. 6, the tube is dropped.

It is preferable that the end parts of the first holding arm 722 and the second holding arm 732 each are formed in an L shape so as to sandwich the knob parts of the holding knobs 444 and 445 that are arranged to face the radial direction of the centrifugal separator 47 and the socket ring 45. By simultaneously disposing the tubes on the centrifugal separator 47 and the socket ring 45, it is possible to perform the disposal operation in half the time required to separately dispose the tubes. Furthermore, by setting the tube holding part 44 of the centrifugal separator 47 to a position so as not to be aligned with the tube holding part 44 of the socket ring 45 in the radial direction, it is possible to selectively dispose the tube only on the socket ring 45.

The support column 76 is fixed on the outer edge of the tube socket base 41. Alternatively, it may be fixed on the intermediate base.

The holding knob operation part 7 is connected with the control device 16 which will be described later, and the driving of the rotary solenoid 74 and the translation solenoid 75 is controlled.

Although it has been described that the holding knob operation part 7 opens and closes the holding arms using the rotary solenoid 74, the holding arms may be opened and closed using a simple structure such as a motor.

The dispensing arm 8 has a dispensing nozzle 81 and dispenses a buffer solution from the dispensing nozzle 81. The dispensing arm 8 is installed on the tube socket base 41.

As shown in FIG. 2, the dispensing nozzle 81 at the end of the dispensing arm 8 is positioned above the tube holding part 44 installed at the outer circumferential part of the centrifugal separator 47. The dispensing nozzle 81 dispenses a buffer solution from above to the specimen in the centrifugal tube held by the tube holding part 44. The dispensing nozzle 8 is connected with a buffer solution tank via a buffer solution pump which will be described later. By controlling the pressure of the buffer solution pump, the amount of buffer solution dispensed into the centrifuge tube is controlled.

The disposal part 9 is a part for disposing the tip T attached to the tip of the pipettor's nozzle 39 of the pipettor arm 3 and the centrifugal tube C3 or the magnetic bead tube C4 held by the tube holding part 44 of the rotary tube socket 4. The disposal part 9 in the processing area is connected with the disposal area.

As shown in FIGS. 1 and 2, the disposal part 9 includes a first disposal port 91 for disposing tips and a second disposal port 92 for disposing tubes. The first disposal port 91 is provided with a waste liquid port 93 for disposing excess specimen (solution) remaining in the tip.

As shown in FIG. 2, the first disposal port 91 is provided within a movable range of the pipettor arm and at a position other than the position where the rotary tube socket is arranged.

Figure 9:
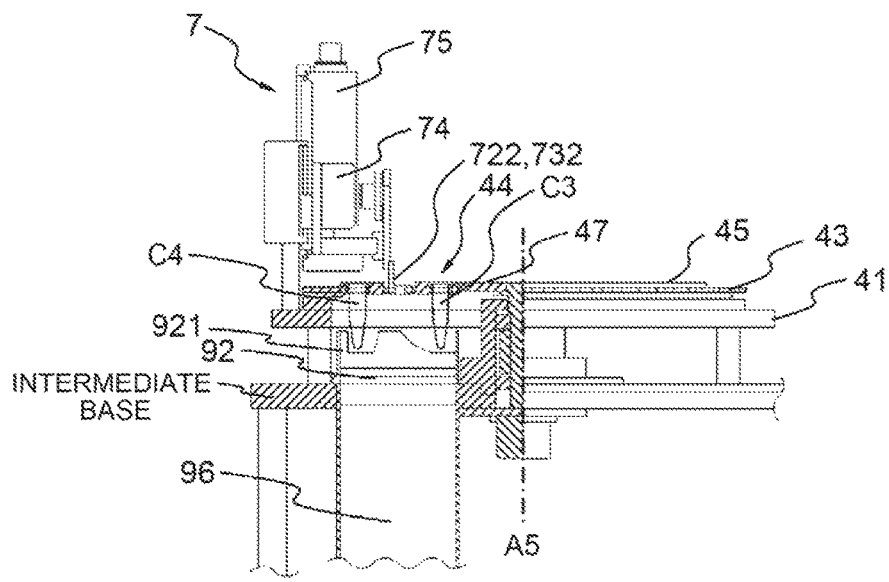
FIG. 9 is cross-sectional view showing an example of a section of the Y line segment in FIG. 4 when viewed from the X direction.

FIG. 9 is a cross-sectional view showing an example of a section of the Y line segment in FIG. 4 when viewed from the X direction. As shown in FIGS. 4 and 9, the second disposal port 92 is provided below the holding knob operation part 7. The second disposal port 92 has the opening width at which the magnetic bead tube C4 installed at the tube holding part 44 of the socket ring 45 and the centrifugal tube C3 installed at the tube holding part 44 of the centrifugal separator 47 can be vertically dropped downward when the two tubes are aligned in the radial direction of rotation. In the second disposal port 92, a disposal guide 921 is provided between the intermediate base and the tube socket base 41, and reliably guides the tube to be disposed to the second disposal port 92. The disposal guide 921 is provided with notches for the centrifugal tube C3 and the magnetic bead tube C4 to rotate and pass. The first disposal port 91 and the second disposal port 92 are connected with a waste liquid pipe and a disposal duct in the disposal area by piercing the intermediate base.

Next, the disposal area will be described in detail. The disposal area is provided in the lower layer of the intermediate base, and at the place where tips, tubes, specimen solutions, and the like which are thrown into from the disposal part 9 are collected. As shown in FIGS. 1 and 2, at the disposal area, a waste liquid pipe 94 connected with the waste liquid port 93, a first waste duct 95 connected with the first disposal port 91, and a second waste duct 96 connected with the second disposal port 92, a waste liquid tank 97 for storing the waste liquid having passed through the waste liquid pipe 94, and a collection box 98 for storing the tips, tubes, and the like having passed through the first waste duct 95 and the second waste duct 96, are provided. A waste gate G5 is further provided for connecting the disposal area with the outside of the apparatus. The operator carries out the waste liquid tank 97 and the collection box 98 in which the wastes are collected in the disposal area from the waste gate G5. The opening and closing of the waste gate G5 can be operated through the operation panel P provided outside the apparatus.

Next, the control area will be described in detail. The control area is provided in the lower layer of the intermediate base and is an area for conveying the first to fourth cartridges, opening and closing the first to fourth gates, controlling the pipettor arm 3, the tube arm 2, the rotary tube socket 4, the holding knob operation part 7, and the pressure of the pipettor arm 3.

As shown in FIG. 1, the control area is provided with a liquid transporting part 15 and a control device 16.

Figure 10:
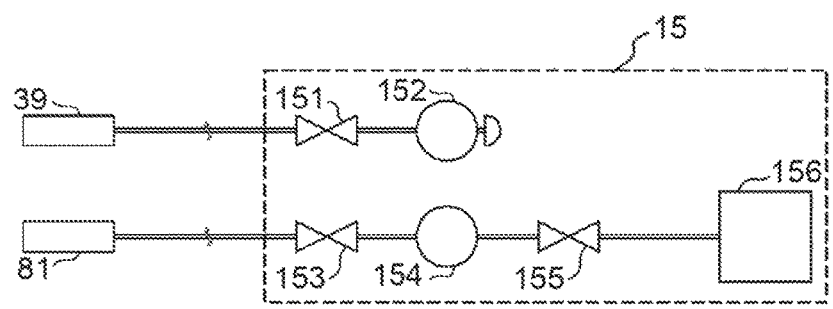
FIG. 10 is a block diagram showing an example of a liquid transporting part.

FIG. 10 is a block diagram showing an example of the liquid transporting part 15. As shown in FIG. 10, the liquid transporting part 15 includes a first electromagnetic valve 151, a cylinder pump 152 for pipettor connected with the first electromagnetic valve 151, a second electromagnetic valve 153, a buffer solution pump 154 connected with the second electromagnetic valve 153, a third electromagnetic valve 155 connected with the buffer solution pump 154, and a buffer solution tank 156 connected with the third electromagnetic valve 155. The first electromagnetic valve 151 is connected with the pipettor's nozzle 39, and the second electromagnetic valve 153 is connected with the dispensing nozzle 81.

The pipettor's nozzle 39 installed at the pipettor arm 3 is connected with the cylinder pump 152 for pipettor via a flexible pipe and the first electromagnetic valve 151, and sucks and discharges the specimen solution through the tip T attached to the pipettor's nozzle 39 by the combined operation of the first electromagnetic valve 151 and the cylinder pump 152 for pipettor.

The dispensing nozzle 81 installed at the dispensing arm 8 is connected with the buffer solution pump 154 via a flexible pipe and the second electromagnetic valve 153, and the buffer solution pump 154 is connected with the buffer solution tank 156 via the flexible pipe and the third electromagnetic valve 155. By the combined operation of the second electromagnetic valve 153, the third electromagnetic valve 155, and the buffer solution pump 154, the buffer solution in the buffer solution tank 156 can be discharged from the dispensing nozzle 81.

Figure 11:
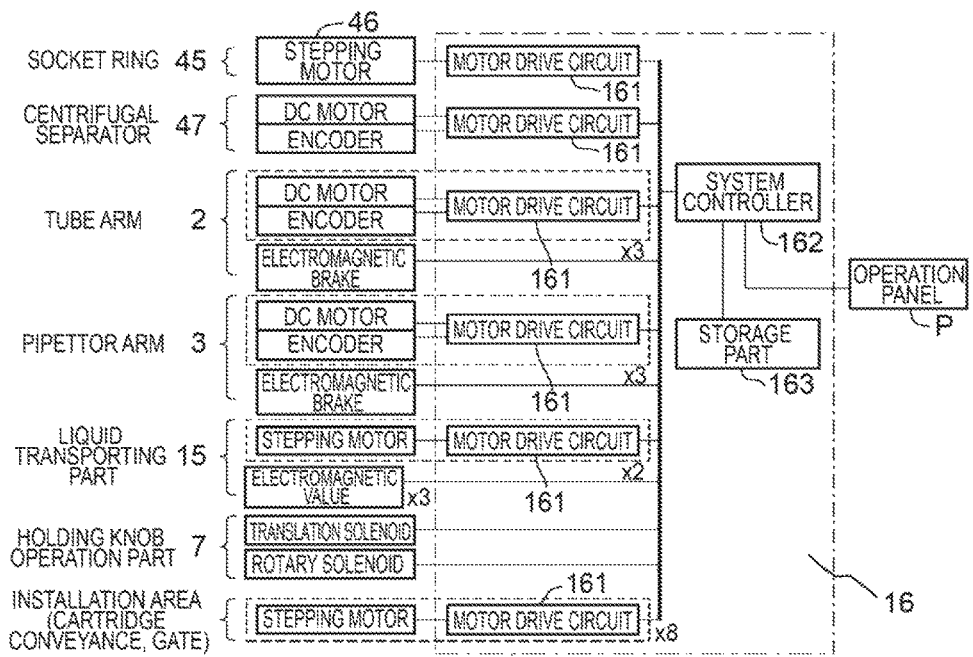
FIG. 11 is a block diagram showing an example of a control device.

FIG. 11 is a block diagram showing an example of the control device 16. As shown in FIG. 11, the control device 16 includes a motor drive circuit 161, a system controller 162 which transmits a command signal to the motor drive circuit 161, and a storage part 163 which stores a driving procedure and a drive log. The motor drive circuit 161 drives the socket ring 45, the centrifugal separator 47, the tube arm 2, the pipettor arm 3, the liquid transporting part 15, the first to fourth cartridges 11~14, the first to fourth gates G1~G4, and a conveying gate.

The fifth motor 46 for rotating the socket ring 45 is controlled by the motor drive circuit 161 provided in the control device 16 to a desired target angle based on a command signal transmitted from the system controller 162. The sixth motor for rotating the centrifugal separator 47 is controlled by the motor drive circuit 161 provided in the control device 16 to a target angular velocity and a target angle based on a sixth encoder signal and a command signal transmitted from the system controller 162.

The first motor 24 and the second motor 27 for driving the links of the tube arm 2, and the linear motion motor for driving the first linear motion mechanism 22, are controlled by the motor drive circuit 161 connected therewith to a desired target angle based on an encoder signal for each motor and a command signal transmitted from the system controller 162. Furthermore, an electromagnetic brake installed at the first linear motion mechanism 22 allows the first linear motion mechanism 22 to operate by releasing the electromagnetic brake during the operation, and functions to prevent the first linear motion mechanism 22 from descending by its own weight when the power is off. The third motor 34 and the fourth motor 37 for driving the links of the pipettor arm 3, and the linear motion motor for driving the second linear motion mechanism 32, are controlled by the motor drive circuit 161 connected therewith to a desired target angle based on an encoder signal for each motor and a command signal transmitted from the system controller 162. Furthermore, an electromagnetic brake installed at the second linear motion mechanism allows the second linear motion mechanism 32 to operate by releasing the electromagnetic brake during the operation, and functions to prevent the second linear motion mechanism 32 from descending by its own weight when the power is off.

The cylinder pump 152 for pipettor and the buffer solution pump 154 provided in the liquid transporting part 15, adjust the sucking/discharging amount by a cylinder driven by a stepping motor. The command signal of each electromagnetic valve is transmitted from the system controller 162.

The translation solenoid 75 and the rotary solenoid 74 provided at the holding knob operation part 7 operate according to a command signal from the system controller 162.

The drive circuit for controlling the stepping motor which drives the first to fourth cartridges, the first to fourth gates, and the conveying gates is also provided in the control device.

The system controller 162 generates a screen of the operation panel P for the operator to input and output information, and acquires the input information. The system controller 162 transmits a command signal to an electric component such as a motor drive circuit or a solenoid based on, for example, the information input to the operation panel.

The operation panel P may take a method of inputting from a monitor of a computer or the like, or may be a touch panel or the like.

The system controller 162 is equivalent to a digital signal processor (DSP) or a central processing unit (CPU), calculates sensor data and encoder data, and generates command signals.

The storage part 163 stores data such as an operation processing procedure, an operation program, an operation log, which can be appropriately read depending on the situation. The storage part may be a tape system such as a magnetic tape or a cassette tape, a disk system including a magnetic disk such as a floppy (registered trademark) disk or a hard disk and an optical disk such as a CD-ROM, an MO, an MD, a DVD or a CD-R, a card system such as an IC card (including a memory card) or an optical card, or a semiconductor memory system such as a mask ROM, an EPROM, an EEPROM, or a flash ROM.

Next, an example of the operation of the automatic container processing apparatus 1 according to the present embodiment will be described.

Figure 12:
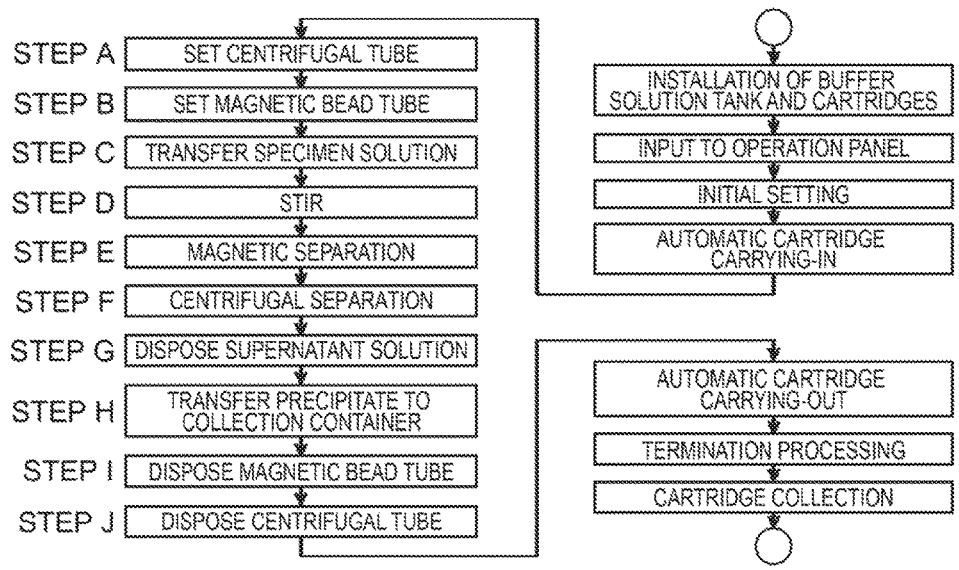
FIG. 12 is a flowchart showing an example of an operation of the automatic container processing apparatus.

FIG. 12 is a flowchart showing an example of the operation of the automatic container processing apparatus. As shown in FIG. 12, the operator installs a buffer solution tank first, and installs the first cartridge 11 loaded with the specimen container C1 (containing the specimen) and the collection container C2, the second cartridge 12 loaded with the tip T, the third cartridge 13 loaded with the centrifugal tube C3, and the fourth cartridge 14 loaded with the magnetic bead tube C4 on the cartridge conveying mechanism at the installation area. Then, each cartridge is automatically carried in the processing area.

The operator instructs to designate processing and to start the automatic operation through the operation panel P, and the automatic processing is started at the processing area.

In step A, the tube arm 2 takes out the centrifugal tube C3 from the third cartridge 13 and transfers it to the centrifugal separator 47. The centrifugal tube C3 is installed at the tube holding part 44 of the centrifugal separator 47.

In step B, the tube arm 2 takes out the magnetic bead tube C4 from the fourth cartridge 14, transfers it to the socket ring 45 of the rotary tube socket 4, and places the magnetic bead tube C4 at the tube holding part 44 of the socket ring 45.

In step C, the socket ring 45 rotates to move the magnetic bead tube C4 to an injection position. The injection position is a position where the specimen is injected from the tip T by the pipettor arm 3. The pipettor arm 3 moves above the second cartridge 12, attaches the tip T, and moves above the specimen container C1 of the first cartridge 11. The specimen is sucked from the specimen container C1 by the cylinder pump 152 for pipettor. The pipettor arm 3 moves above the magnetic bead tube C4 set at the socket ring 45. The specimen is discharged to the magnetic bead tube C4 by the cylinder pump 152 for pipettor, and is injected into the magnetic bead tube C4. The pipettor arm 3 moves to the tip removing jig J to dispose the tip T.

In step D, the socket ring 45 of the rotary tube socket 4 moves the magnetic bead tube C4 to a stirring position, and the stirrer 6 stirs the specimen to mix the specimen with the magnetic beads.

In step E, the socket ring 45 moves the magnetic bead tube C4 to a position of the magnetic separator 5, and a magnetic field is applied. The magnetic beads adsorbing unnecessary substances are gathered around the electromagnet of the magnetic separator. The socket ring 45 moves the magnetic bead tube C4 to the injection position. The pipettor arm 3 moves above the second cartridge 12, attaches the tip T, and moves above the magnetic bead tube C4. The specimen is sucked from the magnetic bead tube C4 by the cylinder pump 152 for pipettor, and the magnetic beads fixed by the magnetic separator 5 remain in the magnetic bead tube C4. Unnecessary substances have been eliminated from the sucked specimen by the magnetic separation.

The pipettor arm 3 moves the sucked specimen to the centrifugal tube C3 set at the centrifugal separator 47. The cylinder pump 152 for pipettor discharges the specimen to the centrifugal tube C3. The pipettor arm 3 moves to the tip removing jig J to dispose the tip T.

In step F, the centrifugal separator 47 rotates to perform centrifugal separation so that the target specimen is precipitated and the supernatant is to be an unnecessary solution.

In step G, the centrifugal separator 47 moves the centrifugal tube C3 to a suction position. The pipettor arm 3 moves above the second cartridge 12, attaches the tip T, and moves above the centrifugal tube C3. The unnecessary supernatant solution is sucked from the centrifugal tube C3 by the cylinder pump 152 for pipettor. The pipettor arm 3 moves above the waste liquid port 93, and the supernatant solution is discharged by the cylinder pump 152 for pipettor and disposed.

In step H, the centrifugal separator 47 moves the centrifugal tube C3 under the dispensing nozzle 81. The buffer solution is dropped from the dispensing nozzle 81 by the buffer solution pump 154. The centrifugal separator 47 transfers the centrifugal tube C3 to the suction position. The pipettor arm 3 moves above the centrifugal tube C3, and the cylinder pump 152 for pipettor sucks the solution containing the precipitate which is the target specimen from the centrifugal tube C3. The pipettor arm 3 moves above the collection container C2, the cylinder pump 152 for pipettor discharges the solution containing the precipitate to transfer the specimen solution to the collection container C2. The pipettor arm 3 moves to the tip removing jig J to dispose the tip T.

In step I, the socket ring 45 of the rotary tube socket 4 moves the magnetic bead tube C4 under the holding knob operation part 7. The holding knob operation part 7 sandwiches the knob parts of the holding knobs 444 and 445 of the tube holding part 44, and drops the magnetic bead tube C4 to dispose it.

In step J, the centrifugal separator 47 moves the centrifugal tube C3 under the holding knob operation part 7. The holding knob operation part 7 sandwiches the knob parts of the holding knobs 444 and 445 of the tube holding part 44, and drops the centrifugal tube C3 to dispose it. Steps I and J may be performed simultaneously or reversely.

After steps A to J are repeated the specified number of times, the automatic processing is terminated.

Each cartridge is automatically carried out to the installation area by the cartridge carrying mechanism.

The operator opens the installation gate G through the operation panel P, and collects the cartridge.

Next, the timing of disposing the magnetic bead tube C4 used for the magnetic separation at the magnetic separator 5 and the centrifugal tube C3 used for the centrifugal separation at the centrifugal separator 47 will be described.

Figure 13A:
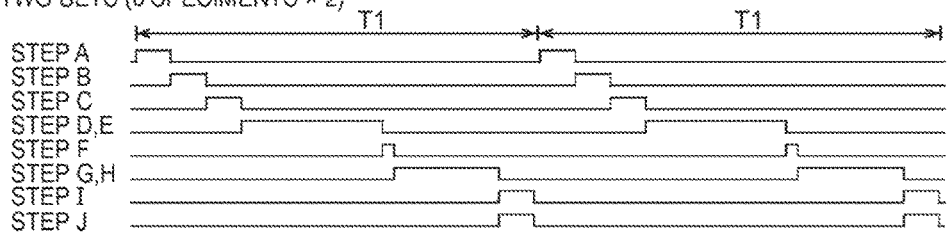
FIGS. 13A and 13B are timing charts of selecting a tube to be disposed used for magnetic separation and centrifugal separation.
Figure 13B:
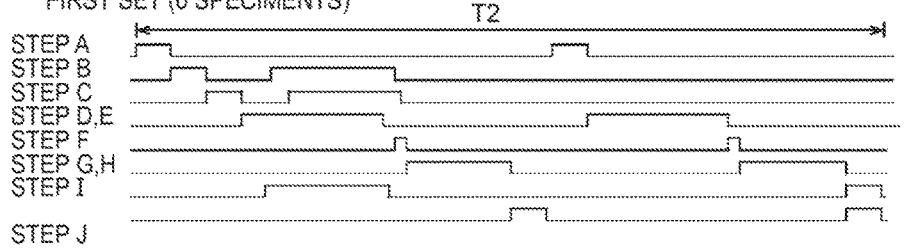

FIGS. 13A and 13B are diagrams showing an example of a timing chart of steps A to J. FIG. 13A is an example of a timing chart of each step in the case where six specimens are one set and two sets of specimens are sequentially processed. In this case, both the magnetic tube and the centrifuge tube of each set can be simultaneously disposed. Since steps I and J are simultaneously performed, it is possible to shorten the tube disposal processing time.

FIG. 13B is an example of a timing chart of each step in the case where the next second set is added during the processing of the first set. In this case, by disposing only the processed magnetic bead tube during the stirring and the magnetic separation are performed to the first set, it is possible to set the second set of the magnetic bead tube and to transfer the specimen to the magnetic bead tube in parallel. Thereafter, the centrifugal separation the transferring the specimen, and the disposal of the centrifuge tube are performed to the first set. Then, the setting the centrifuge tube, and the processing after the stirring, are performed to the second set. It is possible to shorten the time required for setting the magnetic bead tube and for transferring the specimen to the magnetic bead tube of the second set.

It is assumed that the time for processing two consecutive sets is defined as T1×2, and that the time for processing the second set in parallel during the processing of the first set is T2, the expression T2<(T1×2) is established. When two or more sets of specimens are continuously processed while adding specimens, by selectively disposing the centrifuge tube or the magnetic bead tube, it is possible to shorten the processing time.

Since the automatic container processing apparatus according to the present embodiment can drop downward the tube held by the tube holding part of the rotary tube socket and dispose it, it is possible to reduce the risk that contamination is mixed with the collection container and the like from which the processed specimen has been collected. Furthermore, since the processed tube does not pass over the rotary tube socket and is disposed without being raised above the opening of the tube, it is possible to reduce the risk of contamination.

Since the tube holding part has a simple structure that the tube is sandwiched by the holding parts of the two holding knobs, it is possible easily drop the tube to the disposal area by the holding knob operation part.

Furthermore, since the tube holding parts are arranged annularly at the inner side and the outer side of the rotary tube socket, it is possible to design a space-saving and efficient apparatus.

Moreover, by annularly arranging the tube holding parts at the inner side and the outer side, and by arranging the knob parts of the holding knobs of the tube holding parts arranged at the inner side and the outer side so as to face each other, it is possible to simultaneously drop two tubes to the disposal area by the holding knob operation part.

Since the rotary tube socket is constituted by the socket ring which rotates the tube holding part at the outer circumferential position and the centrifugal separator which rotates the tube holding part at the inner circumferential position, the socket ring and the centrifugal separator can be rotationally driven separately, and it is possible to perform different processing at the inner circumferential position and the outer circumferential position. In the present embodiment, it has been exemplified that the rotary tube socket has a double annular structure of the inner and outer sides. However, the rotary tube socket may have a multiple annular structure in which a tube socket is further arranged at the outer circumference. By providing a disposal port according to the size of the multiple annularity and a holding knob operation part, and it is thereby possible to increase the processing amount of specimens and the processing content.

By providing the second disposal port below the holding knob operation part, a horizontal moving mechanism is not required for the holding knob operation part, and it is possible to achieve a space-saving and simple configuration.

Furthermore, by arranging the magnetic separator and the stirrer in the vicinity of the magnetic bead tube installed at the tube holding part of the socket ring, it is possible to perform specimen processing with less influence of contamination.

Second Embodiment

An automatic container processing apparatus according to a second embodiment will be described with reference to FIGS. 14A and 14B.

Figure 14A:
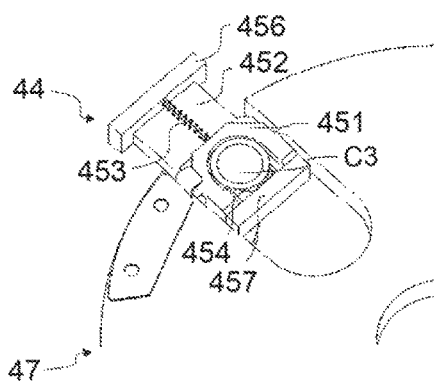
FIGS. 14A and 14B are diagrams schematically showing a tube holding part of an automatic container processing apparatus according to a second embodiment.
Figure 14B:
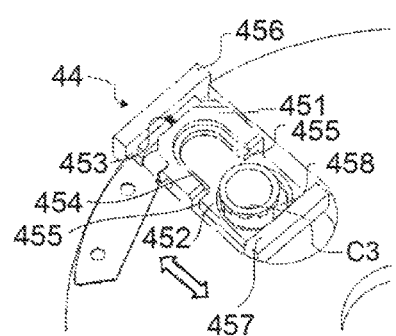

FIGS. 14A and 14B are diagrams schematically showing a tube holding part of the automatic container processing apparatus according to the second embodiment. As shown in FIGS. 14A and 14B, the configurations of a tube holding part 44 and a holding knob operation part 7 are partially different from those of the automatic container processing apparatus according to the first embodiment. The other configurations are the same as those of the automatic container processing apparatus according to the first embodiment.

The tube holding part 44 according to the second embodiment includes a container holding plate 451 for holding a tube, a slide plate 452, and a spring 453 connecting the container holding plate 451 with the slide plate 452.

The container holding plate 451 is provided with a C-shaped notch 454 according to the shape of a centrifugal tube C3 and a guide 455 with which the slide plate 452 slides in the horizontal direction. The container holding plate 451 is installed at the outer circumferential part of a centrifugal separator 47 or the inner circumferential part of a socket ring 45. The centrifugal tube C3 can be placed on the notch 454. The notch 454 is directed toward the center direction (also referred to as a first direction) of the centrifugal separator 47 when installed at the centrifugal separator 47 as shown in FIGS. 14A and 14B, or is directed in the direction opposite to the first direction when installed at the socket ring. The first direction is a direction horizontally directed to the central axis (fifth rotation shaft A5) direction of the centrifugal separator 47.

The slide plate 452 is inserted into the guide 45 of the container holding plate 451 and slides in the first direction or the direction opposite to the first direction. The slide plate 452 is provided with a first stopper 456 at one end thereof perpendicular to the first direction, a second stopper 457 and a through hole 458 larger than the maximum diameter of the centrifugal tube C3 at the other end. The first stopper 456 and the second stopper 457 come in contact with the side surfaces of the container holding plate 451 to stop sliding of the slide plate 452. The through hole 458 of the slide plate 452 is positioned to overlap with the notch 454 while the second stopper 457 is being in contact with the side surface of the container holding plate 451. The notch 454 is also referred to as an opening part.

The spring 453 is connected with the side surface of the first stopper 456 and the side surface of the container holding plate 451, and applies elastic force to both side surfaces.

FIG. 14A shows a state in which the tube holding part 44 holds a tube. As shown in FIG. 14A, the second stopper 457 of the slide plate 452 is in the state of being contact with the side surface of the notch 454 of the container holding plate 451 by the elastic force of the spring. The centrifugal tube C3 is held by the notch 454 and the second stopper 457. At this time, the first stopper 456 of the slide plate 452 is protruding from the outer circumferential part of the centrifugal separator 47.

FIG. 14B shows a state in which the tube holding part 44 releases the centrifugal tube C3. As shown in FIG. 14B, when the slide plate 452 is pushed in the first direction from the holding state of the centrifugal tube C3, the centrifugal tube C3 is pulled out from the notch 454 of the container holding plate 451 together with the through hole 458. As described above, since the diameter of the through hole 458 is larger than the maximum diameter of the tube, the centrifugal tube C3 is dropped downward. The centrifugal tube C3 is disposed in this manner.

A similar mechanism can be used for the tube holding part 44 installed at the socket ring 45.

By pushing the first stoppers 456 of the tube holding parts 44 installed at the centrifugal separator 47 and the socket ring 45 by the opening and closing operations of the holding arms of the holding knob operation part 7, it is possible to simultaneously drop the two tubes. In this case, it is preferable that the holding knob operation part 7 is rotated by 90° about the vertical direction compared with the holding knob operation part of the first embodiment. Thus, the first stopper 456 can be pushed in by the opening operation of the holding arms. At this time, the first stopper of the tube holding part 44 installed at the outer circumferential part of the centrifugal separator 47 and the first stopper of the tube holding part installed at the outer circumferential part of the socket ring are arranged so as to face each other.

It is preferable that wide notches are provided at the outer circumferential part of the centrifugal separator 47 and at the inner circumferential part of the socket ring 45 so that the slide plate 452 can slide with a margin.

Third Embodiment

An automatic container processing apparatus according to a third embodiment will be described with reference to FIGS. 15A and 15B.

FIGS. 15A and 15B are diagrams schematically showing a tube holding part 44 of the automatic container processing apparatus according to the third embodiment. As shown in FIGS. 15A and 15B, the configurations of the tube holding part 44 and a holding knob operation part 7 are different from those of the automatic container processing apparatus according to the first embodiment. The other configurations are the same as those of the automatic container processing apparatus according to the first embodiment.

The tube holding part 44 according to the third embodiment includes a supporting part 461, a first holding plate 462 and second holding plate 463 each for holding a centrifugal tube C3, and a spring (not shown) for energizing each of the first holding plate and the second holding plate.

The supporting part 461 is provided with a C-shaped notch 464. The diameter of the notch is larger than the maximum diameter of the tube. The supporting part 461 serves as a stopper for regulating the rotation of the first holding plate 462 and the second holding plate 463. The supporting part 461 is installed at the outer circumferential part of a centrifugal separator 47 or the inner circumferential part of a socket ring 45.

Each of the first holding plate 462 and the second holding plate 463 is provided with a notch 465 according to the shape of the centrifugal tube C3, and the tube is held by the notches in other words, the first holding plate and the second holding plate are arranged substantially in contact with each other in a plane substantially horizontal to the vertical direction (a slight gap may be provided). While they are being arranged in a horizontal plane, the notches 465 have a shape slightly smaller than the cross-sectional shape of the tube. The supporting part 461, and the first holding plate 462 and the second holding plate 463 are arranged in contact with each other. The C-shaped notch 464 of the supporting part 461 and the notches 465 of the first holding plate 462 and the second holding plate 463 are arranged so that their positions are substantially matched. As shown in FIG. 15A, each of the first holding plate and the second holding plate has a rotation shaft A7 at its end, and rotates about the rotation shaft. The direction of the rotation shaft is, for example, substantially the center direction of the centrifugal separator 47. While rotating, the first holding plate 462 and the second holding plate 463 in the present embodiment are in a state of what is called double doors opening outward.

A spring (not shown) is connected with each of the first holding plate 462 and the second holding plate 463. The springs connected with the first holding plate 462 and the second holding plate 463 energize the first holding plate and the second holding plate in a direction contacting the supporting part 461. By the action of the springs, the first holding plate 462 and the second holding plate 463 keep the state of holding the centrifugal tube C3.

When the tube holding part of the present embodiment is opened, by pushing the adjacent position of the first holding plate 462 and the second holding plate 463 downward, the first holding plate 462 and the second holding plate 463 are opened downward, and the tube is dropped.

In order to open the tube holding part and drop the tube, the adjacent position of the first holding plate 462 and the second holding plate 463 is pushed down by the holding arms of the holding knob operation part 7.

Alternatively, a rod body 733 shown in FIG. 15B may be used instead of the holding arms of the holding knob operation part 7. As shown in FIG. 8, an L-shaped holding mechanism base 71 formed of two surfaces of a vertical surface and a horizontal surface is connected with one end of a tension spring 763 of which the other end is connected with a support plate 761. The holding mechanism base 71 is lowered by being pushed downward by a pushing in-pulling out rod 751 of a translation solenoid 75, and raised by the pullback of the pushing in-pulling out rod 751 and the restoring force of the tension spring 763. The translation solenoid 75 is supported by the support plate 761 fixed to a support column 76. A support block 762 fixed to the support column 76 is provided with a second rail R2 which guides the holding mechanism base 71 in the vertical direction, and is connected with a link guide provided on the vertical surface of the holding mechanism base 71. The holding mechanism base 71 moves along the second rail R2 in the vertical direction according to the driving of the translation solenoid 75. A rotation motor having a rotation shaft in the vertical direction is provided on the horizontal surface of the holding mechanism base 71, and the rod body 733 is connected with the rotation shaft of the motor.

FIG. 15B is a view showing the position of the rod body 733 when the first holding plate 462 and the second holding plate 463 of the tube holding part 44 are pushed down.

The rod body 733 has, for example, a quadrangular prism shape having first to fourth side surfaces. The first side surface P1 has a first protrusion 771. The second side surface P2 has a second protrusion 772, and the third side surface P3 has a third protrusion 773. The second protrusion 772 and the third protrusion 773 have the same height. The first protrusion 771 has a different height from the second and third protrusions 772 and 773. The rod body 733 has a mechanism for moving upward and downward in the height direction and for rotating about the longitudinal direction. When a tube of either of the tube holding parts 44 installed at the outer circumferential part of the centrifugal separator 47 or at the inner circumferential part of the socket ring 45 is to be dropped, the first holding plate 462 and the second holding plate 463 are pushed down by the first protrusion 771. When the tubes of both tube holding parts 44 are to be dropped, the rod body 733 is rotated by 90°, two pairs of the first holding plate 462 and the second holding plate 463 are pushed down by the second protrusion 772 and the third protrusion 773.

With the tube holding part 44 according to the present embodiment, it is possible to drop the centrifugal tube C3 downward from the tube holding part 44 only by the pushing operation of the holding knob operation part 7. Consequently, it is possible to simplify the configuration of the holding knob operation part 7. When the tube C4 installed at the tube holding part 44 of the socket ring 45 and the centrifugal tube C3 installed at the tube holding part 44 of the centrifugal separator 47 are aligned in the radius direction of rotation, it is possible to simultaneously dispose the two tubes, or to selectively dispose either one. As a result, it is possible to set the rotational positions of the socket ring 45 and the centrifugal separator 47 in the magnetic separation, the stirring, and the dispensing without restricted by the dispose position.

Fourth Embodiment

An automatic container processing apparatus according to a fourth embodiment will be described with reference to FIG. 16.

FIG. 16 is a diagram schematically showing a holding knob operation part 7 of the automatic container processing apparatus according to the fourth embodiment. As shown in FIG. 16, the configuration of the holding knob operation part 7 is different from that of the automatic container processing apparatus according to the first embodiment. The other configurations are the same as those of the automatic container processing apparatus according to the first embodiment.

The holding knob operation part 7 according to the fourth embodiment includes a manipulator mechanism 723 as a first holding link and a second holding link. As shown in FIG. 16, the manipulator mechanism 723 is attached to a first holding arm 722 and a second holding arm 732. In the present embodiment, by using the manipulator mechanism 723, expansion and contraction, and opening and closing of the holding arms of the holding knob operation part 7 can be simultaneously performed. Because the holding arms can be expanded and contracted in the vertical direction, the translation solenoid is not required. Thus, it is possible to simplify the configuration of the holding knob operation part and contribute to cost reduction.

Fifth Embodiment

An automatic container processing apparatus according to a fifth embodiment will be described with reference to FIG. 17.

Figure 17:
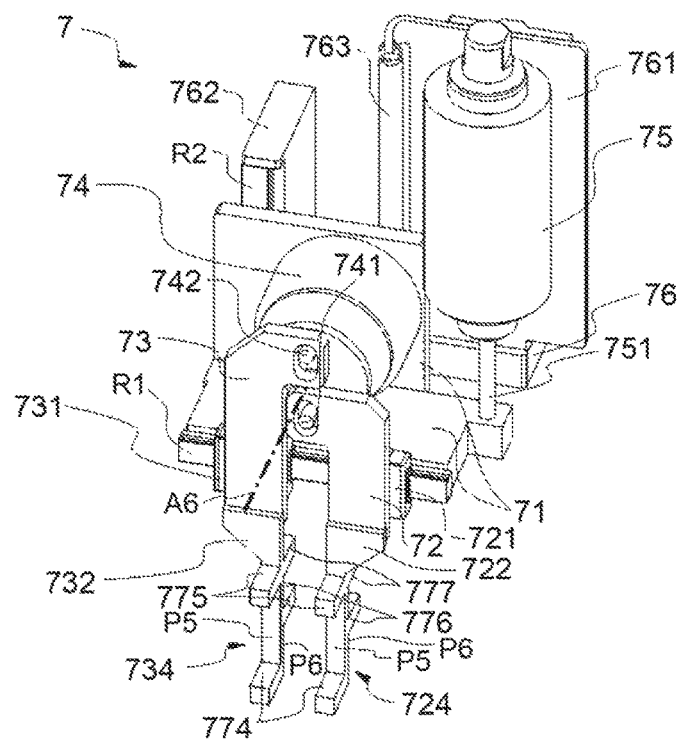
FIG. 17 is a diagram schematically showing a holding knob operation part of an automatic container processing apparatus according to a fifth embodiment.

FIG. 17 is a diagram schematically showing a holding knob operation part 7 of the automatic container processing apparatus according to the fifth embodiment. As shown in FIG. 17, the configuration of the holding knob operation part 7 is different from that of the automatic container processing apparatus according to the first embodiment. The other configurations are the same as those of the automatic container processing apparatus according to the first embodiment.

The holding knob operation part 7 according to the fifth embodiment has a plurality of protrusions on a first end part 724 of a first holding arm 722 and a second end part 734 of a second holding arm 732.

The first end part 724 has a quadrangular prism shape, and has a fifth side surface P5 facing the centrifugal separator and a sixth side surface P6 which is the side surface opposite to the fifth side surface P5. The fifth side surface P5 has a fourth protrusion 774 and a fifth protrusion 775 which have a different height. The fourth protrusion 774 and the fifth protrusion 775 are perpendicular to the fifth side surface P5. The sixth side surface P6 has a sixth protrusion 776 having a different height from the fourth protrusion 774 and the fifth protrusion 775, and a seventh protrusion 777 having the same height as the fifth protrusion 775. The sixth protrusion 776 and the seventh protrusion 777 are perpendicular to the sixth side surface P6.

The second end part 734 has a quadrangular prism shape which is the same shape as the first end part 724.

As shown in FIG. 17, while the first holding arm 722 and the second holding arm 732 are being closed, the fourth to seventh protrusions have the sage height respectively.

When tubes are dropped by sandwiching the holding knobs of the tube holding parts 44 installed at the centrifugal separator 47 and at the socket ring 45, the first holding arm 722 and the second holding arm 732 can select which protrusions to sandwich the holding knobs by changing the height of the holding arms by the translation solenoid 75. Specifically, since the heights of the protrusions provided at the first end part 724 and the second end part 734 are different in three levels the protrusion having suitable height is selected from the three levels. The translation solenoid 75 can be positioned at three points.

When only the holding knobs of the tube holding part 44 installed at the outer circumferential part of the centrifugal separator 47 are to be sandwiched, the translation solenoid 75 is driven so that the holding knobs are to be at the height of the fourth protrusion 774. Then, by closing the first holding arm 722 and the second holding arm 732, and by sandwiching the holding knobs with the respective fourth protrusions 774, the tube is dropped from the tube holding part 44.

When only the holding knobs of the tube holding 44 installed at the inner circumference part of the socket ring 45 is to be sandwiched, the translation solenoid 75 is driven so that the holding knobs are to be at the height of the sixth protrusion 776. Then, by closing the first holding arm 722 and the second holding arm 732, and by sandwiching the holding knobs with the respective sixth protrusions 776, the tube is dropped from the tube holding part 44.

When the holding knobs of both the tube holding part 44 installed at the outer circumferential part of the centrifugal separator 47 and the tube holding part 44 installed at the inner circumferential part of the socket ring 45 are to be simultaneously sandwiched, the translation solenoid 75 is driven so that both holding knobs are to be at the height of the fifth protrusion 775 and the seventh protrusion 777. Then, the first holding arm 722 and the second holding arm 732 are closed, and both holding knobs are sandwiched by the respective fifth protrusions 775 and the respective seventh protrusions 777. Consequently, the tubes are dropped from the two tube holding parts 44.

The order of heights of the fourth protrusion 774, the sixth protrusion 776, the fifth protrusion 775, and the seventh protrusion 777 is not limited as long as the respective heights are not the same, and any protrusion can be at a higher position.

With the holding knob operation part according to the present embodiment, it is possible to selectively dispose the tube of the tube holding part. When a magnetic bead tube C4 installed at the tube holding part 44 of the socket ring 45 and the centrifugal tube C3 installed at the tube holding part 44 of the centrifugal separator 47 are aligned in the radius direction of rotation, it is possible to simultaneously dispose the two tubes, or to selectively dispose either one. As a result, it is possible to set the rotational positions of the socket ring 45 and the centrifugal separator 47 in the magnetic separation, the stirring, and the dispensing without restricted by the dispose position.

Sixth Embodiment

An automatic container processing apparatus according to a sixth embodiment will be described with reference to FIG. 18.

Figure 18:
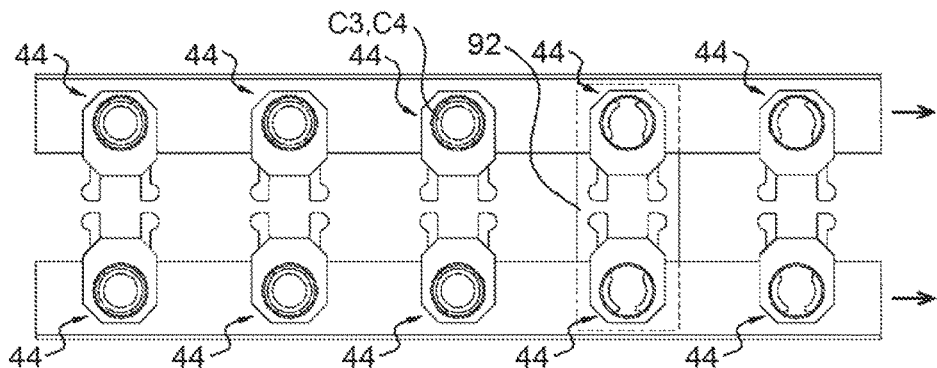
FIG. 18 is a diagram schematically showing an arrangement of tube holding parts of an automatic container processing apparatus according to a sixth embodiment.

FIG. 18 is a diagram schematically showing an arrangement of tube holding parts 44 of the automatic container processing apparatus according to the sixth embodiment. As shown in FIG. 18, the arrangement of the tube holding parts 44 is different from that of the automatic container processing apparatus according to the first embodiment. The other configurations are the same as those of the automatic container processing apparatus according to the first embodiment.

A plurality of tube holding parts 44 according to the sixth embodiment is arranged in two rows in the lateral direction. The tube holding parts 44 in the two rows are arranged so that holding knobs face each other. The two rows of tube holding parts are translatable in the direction of the arrow in FIG. 17, and the second disposal port 92 is installed in the translation path. The tubes to be disposed are conveyed, and the tubes are disposed by the holding knob operation part 7 at the second disposal port 92.

While certain embodiments have been described, these embodiments have been presented by way of examples only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An automatic container processing apparatus comprising:
   a tube socket having a container holding part for holding a container;
   an operation part capable of operating the container holding part of the tube socket;
   a disposal port provided below the tube socket; and
   a control device that controls the operation part,
   wherein
   the tube socket is annular,
   a plurality of container holding parts is annularly arranged, and
   the container held by the container holding part is dropped to the disposal part by operating the operation part.

2. The automatic container processing apparatus according to claim 1, wherein
   the tube socket comprises
   a first tube socket provided at an inner side; and
   a second tube socket provided at an outer side of the first tube socket, and
   the operation part is capable of operating any of a first container holding part of the first tube socket and a second container holding part of the second tube socket.

3. The automatic container processing apparatus according to claim 1, wherein
   the tube socket comprises
   a first tube socket provided at an inner side; and
   a second tube socket provided at an outer side of the first tube socket, and
   the operation part is capable of simultaneously operating both a first container holding part of the first tube socket and a second container holding part of the second tube socket.

4. The automatic container processing apparatus according to claim 3, wherein
   the operation part simultaneously operates both a first knob part of the first container holding part and a second knob part of the second container holding part to drop the respective containers held by the first container holding part and the second container holding part,
   the first knob part and the second knob part are arranged between the first container holding part of the first tube socket and the second container holding part of the second tube socket.

5. The automatic container processing apparatus according to claim 1, wherein
   the container holding part comprises
   at least one pair of holding plates each having a knob part and a holding part for holding the container;
   a holder having a rotating shaft for rotating each of the holding plates and a through hole through which the container passes; and an elastic part which connects the knob parts of the holding plates and energizes an elastic force in a direction separating the knob parts from each other, and when the knob parts are close to each other by the operation part, the holding parts are separated to drop the held container.

6. The automatic container processing apparatus according to claim 5, wherein the operation part comprises an operating arm part which operates the knob part;

an opening and closing drive part which opens and closes the operating arm part; and a moving part which moves the operating arm part close to and away from the knob part.

7. The automatic container processing apparatus according to claim 1, wherein the container holding part comprises a container supporting plate for supporting the container; and a slide plate provided between the tube socket and the container supporting plate, and slidable along a predetermined direction, the container supporting plate has an opening part in the predetermined direction, the slide plate has a through part larger than a diameter of the container, and the operation part slides the slide plate in the predetermined direction to release the container from the opening part of the container supporting plate and to drop the container from the through part.

8. The automatic container processing apparatus according to claim 1, wherein the container holding part comprises at least two container supporting plates for supporting the container, each of the container supporting plates is rotatable downward by a rotation shaft, and the operation part rotates the container supporting plates to drop the container.

9. An automatic container processing apparatus comprising:

a tube socket having a container holding part for holding a container;

an operation part capable of operating the container holding part of the tube socket; and a control device that controls the operation part, wherein the tube socket is annular, a plurality of container holding parts is annularly arranged, the container held by the container holding part is dropped by operating the operation part, the tube socket comprises:

a first tube socket provided at an inner side; and a second tube socket provided at an outer side of the first tube socket, the operation part is capable of operating at least one of a first container holding part of the first tube socket and a second container holding part of the second tube socket.

10. The automatic container processing apparatus according to claim 9, further comprising:

a disposal port provided below the tube socket.

11. An automatic container processing apparatus comprising:

a tube socket having a container holding part for holding a container;

an operation part capable of operating the container holding part of the tube socket; and a control device that controls the operation part, wherein the container held by the container holding part is dropped by operating the operation part, the container holding part comprises:

at least one pair of holding plates each having a knob part and a holding part for holding the container;

a holder having a rotating shaft for rotating each of the holding plates and a through hole through which the container passes; and an elastic part which connects the knob parts of the holding plates and energizes an elastic force in a direction separating the knob parts from each other, and when the knob parts are close to each other by the operation part, the holding parts are separated to drop the held container.

12. An automatic container processing apparatus comprising:

a tube socket having a container holding part for holding a container;

an operation part capable of operating the container holding part of the tube socket; and a control device that controls the operation part, wherein the container held by the container holding part is dropped by operating the operation part the container holding part comprises:

a container supporting plate for supporting the container, and a slide plate provided between the tube socket and the container supporting plate, and slidable along a predetermined direction, the container supporting plate has an opening part in the predetermined direction, the slide plate has a through part larger than a diameter of the container, and the operation part slides the slide plate in the predetermined direction to release the container from the opening part of the container supporting plate and to drop the container from the through part.

13. An automatic container processing apparatus comprising:

a tube socket having a container holding part for holding a container;

an operation part capable of operating the container holding part of the tube socket; and a control device that controls the operation part, wherein the container held by the container holding part is dropped by operating the operation part, the container holding part comprises at least two container supporting plates for supporting the container, each of the container supporting plates is rotatable downward by a rotation shaft, and the operation part rotates the container supporting plates to drop the container.

* * * * *